(12) United States Patent
Han et al.

(10) Patent No.: US 10,231,689 B2
(45) Date of Patent: Mar. 19, 2019

(54) X-RAY IMAGING APPARATUS AND METHOD OF CONTROLLING THE SAME

(71) Applicant: SAMSUNG ELECTRONICS CO., LTD., Suwon-si (KR)

(72) Inventors: Seok Min Han, Seongnam-si (KR); Dong Goo Kang, Hwaseong-si (KR); Young Hun Sung, Hwaseong-si (KR); Jae Hak Lee, Yongin-si (KR); Ji Young Choi, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 409 days.

(21) Appl. No.: 14/910,759

(22) PCT Filed: Aug. 8, 2014

(86) PCT No.: PCT/KR2014/007388
§ 371 (c)(1),
(2) Date: Feb. 8, 2016

(87) PCT Pub. No.: WO2015/020481
PCT Pub. Date: Feb. 12, 2015

(65) Prior Publication Data
US 2016/0192895 A1    Jul. 7, 2016

(30) Foreign Application Priority Data

Aug. 8, 2013    (KR) .................. 10-2013-0093961

(51) Int. Cl.
*A61B 6/00*    (2006.01)

(52) U.S. Cl.
CPC .............. *A61B 6/583* (2013.01); *A61B 6/481* (2013.01); *A61B 6/482* (2013.01); *A61B 6/487* (2013.01); *A61B 6/504* (2013.01); *A61B 6/5211* (2013.01)

(58) Field of Classification Search
CPC ......... A61B 6/481; A61B 6/482; A61B 6/487; A61B 6/504; A61B 6/5211; A61B 6/583
(Continued)

(56) References Cited

U.S. PATENT DOCUMENTS

| 6,404,844 B1 * | 6/2002 | Horiuchi et al. ...... A61B 6/583 378/8 |
| 7,203,270 B2 * | 4/2007 | Okumura et al. .......................... G01N 2223/612 378/16 |

(Continued)

FOREIGN PATENT DOCUMENTS

| JP | 201172818 A | 4/2011 |
| JP | 2011240178 A | 12/2011 |

(Continued)

OTHER PUBLICATIONS

International Search Report dated Nov. 11, 2014, issued by the International Searching Authority in counterpart International Application No. PCT/KR2014/007388 (PCT/ISA/210).

(Continued)

*Primary Examiner* — Gregory F Cunningham
(74) *Attorney, Agent, or Firm* — Sughrue Mion, PLLC

(57) ABSTRACT

Provided is an X-ray imaging apparatus including: an image generation unit configured to generate an X-ray image based on X-rays transmitted by an object; a thickness measurement unit configured to measure thickness information of the object and generate a reference phantom image in which the measured thickness information is indicated; and an image separation unit configured to generate a final image obtained by separating a material inside the object from the X-ray image using the reference phantom image.

14 Claims, 18 Drawing Sheets

(58) Field of Classification Search
USPC .......................................................... 382/128
See application file for complete search history.

(56) References Cited

U.S. PATENT DOCUMENTS

2008/0281181 A1    11/2008  Manzione et al.
2012/0189175 A1*    7/2012  Highnam et al. ..... G06T 7/0012
                                                    382/128

FOREIGN PATENT DOCUMENTS

JP          201290944 A      5/2012
WO          2012082994 A2    6/2012

OTHER PUBLICATIONS

Written Opinion dated Nov. 11, 2014, issued by the International Searching Authority in counterpart International Application No. PCT/KR2014/007388 (PCT/ISA/237).

* cited by examiner

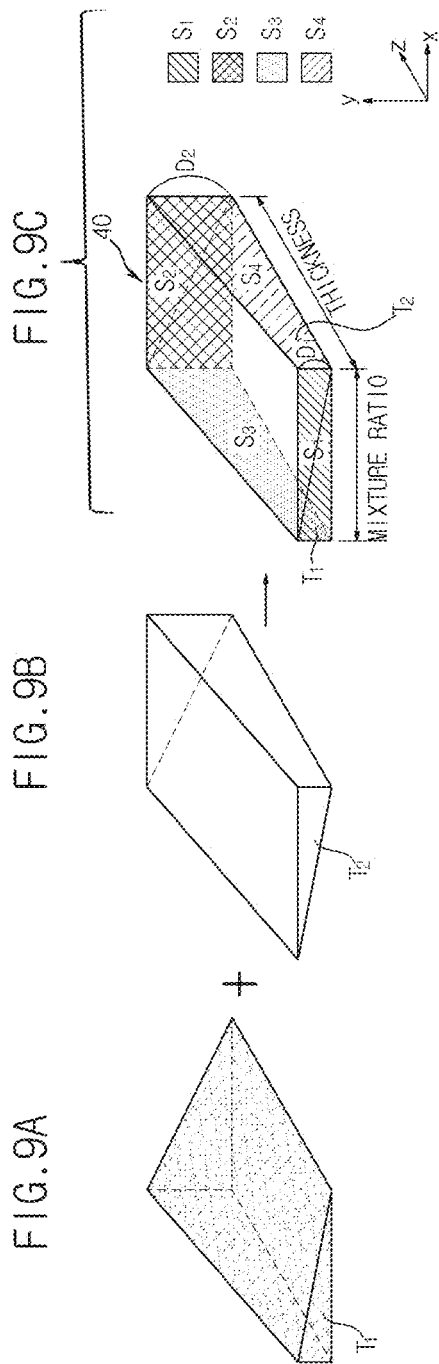

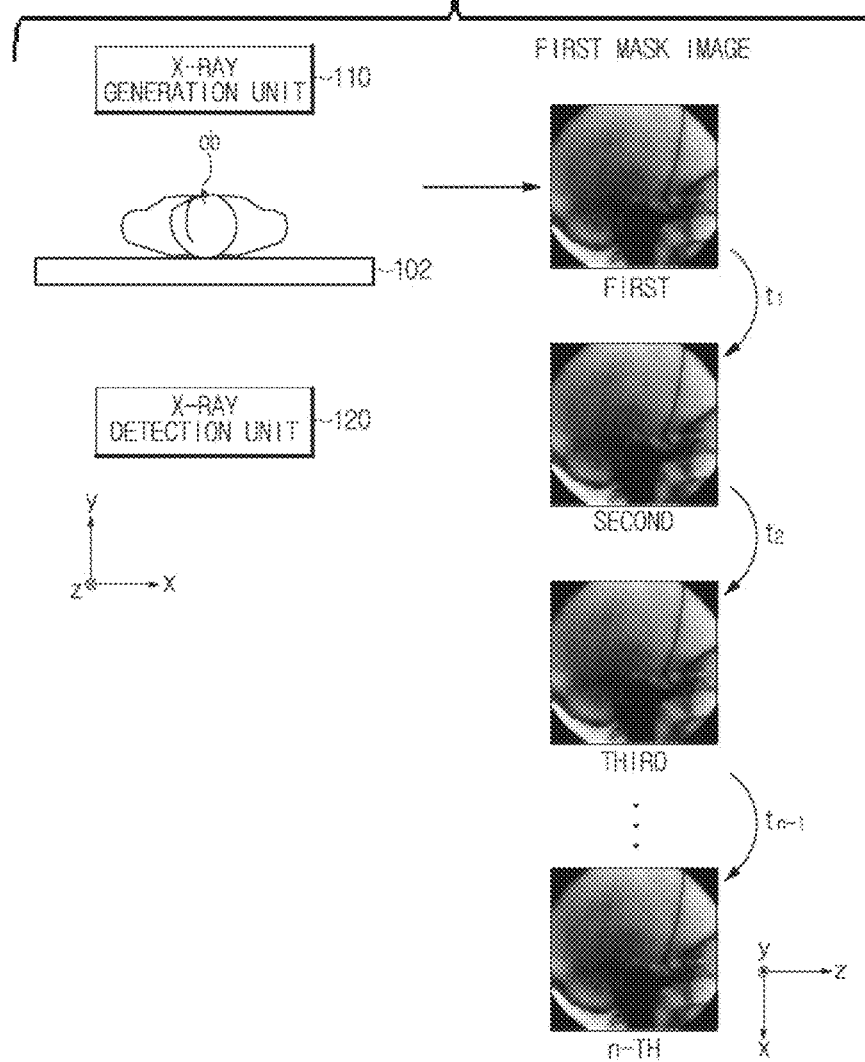

FIG. 14A
FIG. 14B
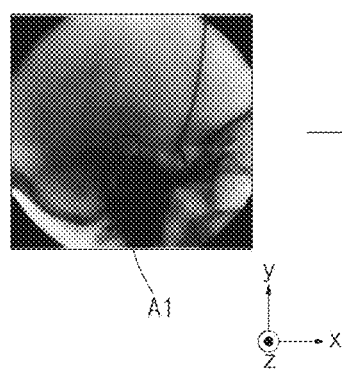
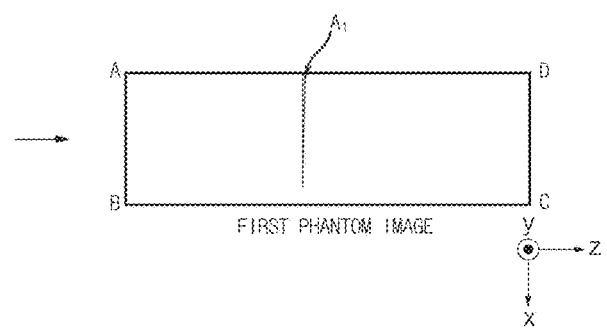
FIRST PHANTOM IMAGE

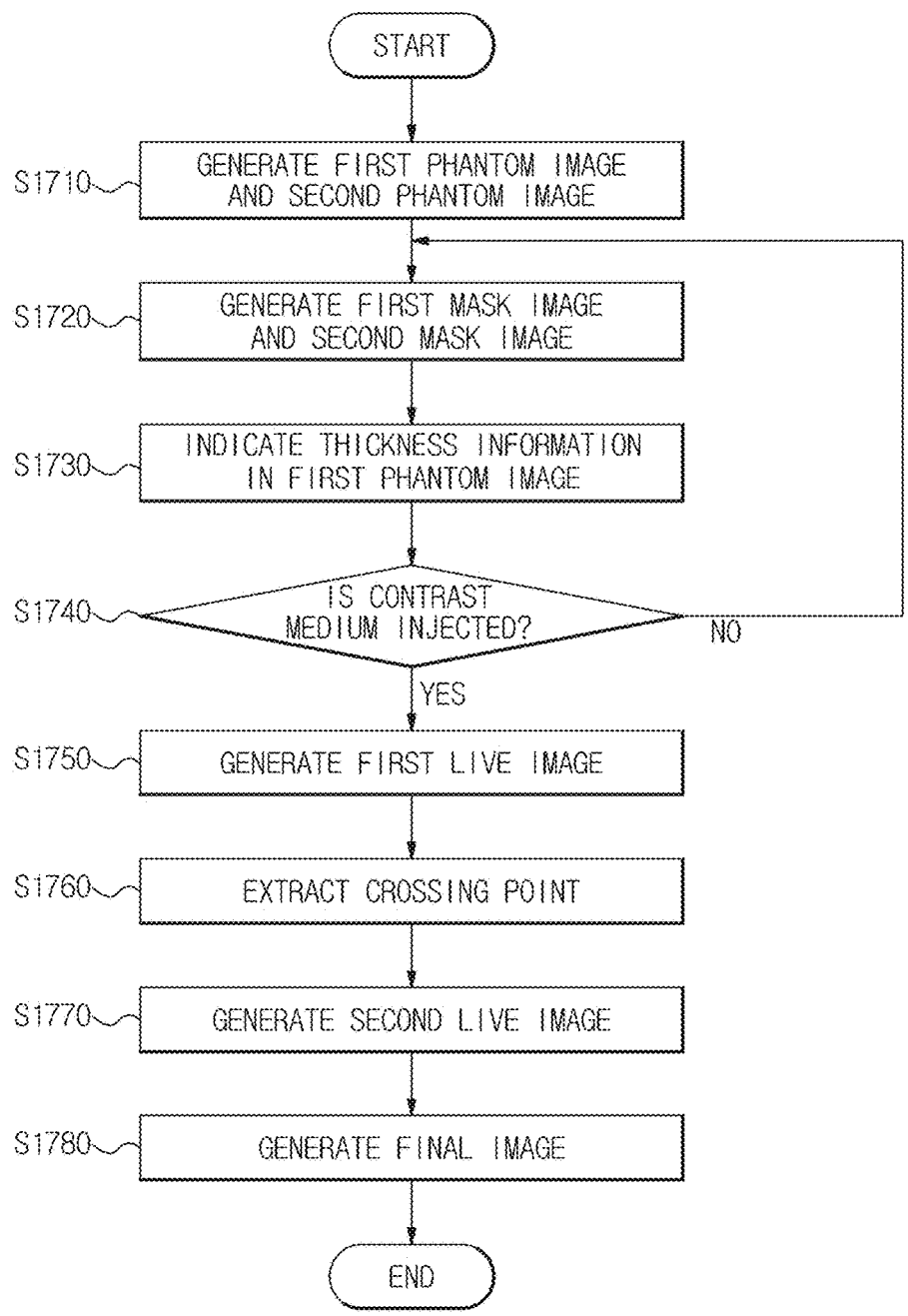

X-RAY IMAGING APPARATUS AND METHOD OF CONTROLLING THE SAME

CROSS-REFERENCE TO RELATED APPLICATION

This is a National Stage Entry of International Application No. PCT/KR2014/007388 filed Aug. 8, 2014, claiming priority based on Korean Patent Application No. 10-2013-0093961 filed Aug. 8, 2013, the contents of all of which are incorporated herein by reference in their entirety.

TECHNICAL FIELD

Embodiments of the present invention relate to an X-ray imaging apparatus and a method of controlling the same, and more particularly, to an X-ray imaging apparatus that is capable of generating an X-ray image that is not affected by the movement of an object and a method of controlling the same.

BACKGROUND ART

X-ray imaging apparatuses are apparatuses that are capable of obtaining an image inside an object by radiating X-rays onto the object and using the X-rays transmitted by the object. Since transmittance of X-rays varies according to the characteristics of a material used to form the object, an internal structure of the object can be imaged by detecting an intensity or strength of the X-rays transmitted by the object.

In detail, when an X-ray generation unit generates X-rays and radiates the X-rays onto the object, an X-ray detection unit detects the X-rays transmitted by the object and converts the detected X-rays into electrical signals. Conversion into the electrical signals is performed in units of pixels, one X-ray image can be obtained by combining an electrical signal corresponding to each pixel.

As a part of the X-ray image, a digital subtraction angiography (DSA) image for a dynamic organ is mainly used. In a method of extracting blood vessels from an angiography image according to the related art, the quality of the image is remarkably lowered, and a severe change of lighting occurs when the X-ray image is obtained. When the DSA image is used, a blood vessel region can be prominently expressed in an image in which a motion artifact and contrast are severe such that these problems can be solved.

DISCLOSURE

Technical Problem

Therefore, it is an aspect of the present invention to provide an X-ray imaging apparatus that is capable of removing a motion artifact that occurs due to the movement of an object, and a method of controlling the X-ray imaging apparatus.

Technical Solution

In accordance with one aspect of the present invention, an X-ray imaging apparatus includes: an image generation unit configured to generate an X-ray image based on X-rays transmitted by an object; a thickness measurement unit configured to measure thickness information of the object and generate a reference phantom image in which the measured thickness information is indicated; and an image separation unit configured to generate a final image obtained by separating a material inside the object from the X-ray image using the reference phantom image.

In accordance with another aspect of the present invention, a method of controlling an X-ray imaging apparatus includes: generating a first phantom image and a second phantom image; generating a first mask image and a second mask image; measuring thickness information of an object; generating a reference phantom image in which the thickness information of the object is indicated; generating a first live image; generating a second live image based on the first live image; and generating a final image using the second live image and the second mask image.

Advantageous Effects

In accordance with the aspect of the present invention, the thickness information of the object ob is firstly measured, and the DSA image of the object ob is obtained based on the thickness information, so that, even when the object ob is moved, a motion artifact may be prevented from occurring in the DSA image.

DESCRIPTION OF DRAWINGS

These and/or other aspects of the invention will become apparent and more readily appreciated from the following description of the embodiments, taken in conjunction with the accompanying drawings of which:

FIGS. 9A through 9C illustrate a structure of a phantom;

FIG. 10 illustrates an operation of generating a mask image;

FIGS. 14A and 14B illustrate a first phantom image in which thickness information of an object is indicated;

FIG. 17 is a flowchart illustrating a method of controlling an X-ray imaging apparatus in accordance with an embodiment of the present invention.

BEST MODE

Figure 1:
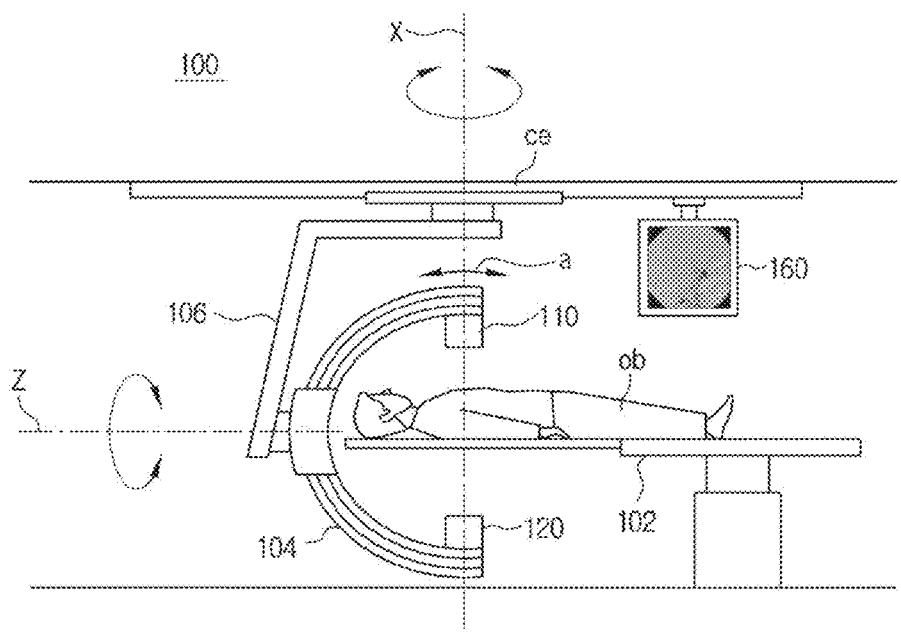
FIG. 1 illustrates the exterior of an X-ray imaging apparatus in accordance with an embodiment of the present invention.

Purposes, particular advantages, and new features of the present invention will be more apparent from the following detailed description and exemplary embodiments associated with the attached drawings. When adding reference numerals to elements of the drawings in the specification, it should be noted that like reference numerals are used for like elements wherever possible even when like elements are shown in different drawings. Also, in the description of the present invention, if it is determined that a detailed description of commonly used technologies or structures related to the invention may unnecessarily obscure the subject matter of the invention, the detailed description will be omitted. It will be understood that although the terms first and second are used herein to describe various elements, these elements should not be limited by these terms. These terms are only used to distinguish one element from another element.

Reference will now be made in detail to the embodiments of the present invention, examples of which are illustrated in the accompanying drawings, wherein like reference numerals refer to like elements throughout.

The structure or photographing method of an X-ray imaging apparatus may vary according to a part to be photographed, the type of an X-ray image, or the purpose of photographing. In detail, there are a general X-ray imaging apparatus that captures an image of a chest, an arm, or a leg, an X-ray imaging apparatus using mammography that is a breast photographing technique, an X-ray imaging apparatus using fluoroscopy, an X-ray imaging apparatus using angiography, an X-ray imaging apparatus for cardiography, and an X-ray imaging apparatus using tomography. Thus, an X-ray imaging apparatus in accordance with an embodiment of the present invention may be any one among the above-described X-ray imaging apparatuses or a combination of two or more X-ray imaging apparatuses.

FIG. 1 illustrates the exterior of an X-ray imaging apparatus in accordance with an embodiment of the present invention.

Referring to FIG. 1, an X-ray imaging apparatus 100 may include an X-ray generation unit 110 and an X-ray detection unit 120 that is disposed to face the X-ray generation unit 110.

The X-ray generation unit 110 may generate X-rays so as to obtain an X-ray image of an object ob and may radiate the generated X-rays onto the object ob.

The X-ray detection unit 120 may detect the X-rays that are radiated by the X-ray generation unit 110 and transmitted by the object ob. Also, the X-ray detection unit 120 may convert the detected X-rays into electrical signals.

Here, the object ob may be the body of a human being or an animal. However, embodiments of the present invention are not limited thereto, and the object ob may be any type of object having an internal structure that may be imaged by the X-ray imaging apparatus 100.

The X-ray imaging apparatus 100 may further include a table 102 on which the object ob is accommodated. Thus, while the X-rays are radiated by the X-ray generation unit 110, the object ob may be accommodated on the table 102 and may be placed between the X-ray generation unit 110 and the X-ray detection unit 120.

As illustrated in FIG. 1, the X-ray generation unit 110 and the X-ray detection unit 120 may be disposed at both facing ends of a C-shaped arm 104. The C-shaped arm 104 is mounted to be rotatable about a horizontal axis indicated by Z. Also, the C-shaped arm 104 may be rotated in a circular or semicircular form in a direction of arrow a. Also, the C-shaped arm 104 may be mounted on a support part 106 installed on a ceiling ce, and the support part 106 may be rotated about a vertical axis indicated by X. Thus, X-ray images may be obtained from various regions of interest (ROIs) of the object ob in various directions through rotation of the C-shaped arm 104 and the support part 106.

An X-ray image of the object ob obtained by performing image processing on the electrical signal of the X-rays detected by the X-ray detection unit 120 may be displayed on a display unit 160. In this case, in FIG. 1, the display unit 160 is installed on the ceiling ce; however, the position of the display unit 160 is not limited thereto.

Although not shown in FIG. 1, the X-ray imaging apparatus 100 may further include an input unit 140. In this case, the input unit 140 may be a switch, a keyboard, a track ball, or a touch screen. However, embodiments of the present invention are not limited thereto.

The display unit 160 may be a cathode ray tube (CRT), a liquid crystal display (LCD) device, a light emitting diode (LED) display device, or an organic light emitting diode (OLED) display device; however, embodiments of the present invention are not limited thereto.

Figure 2:
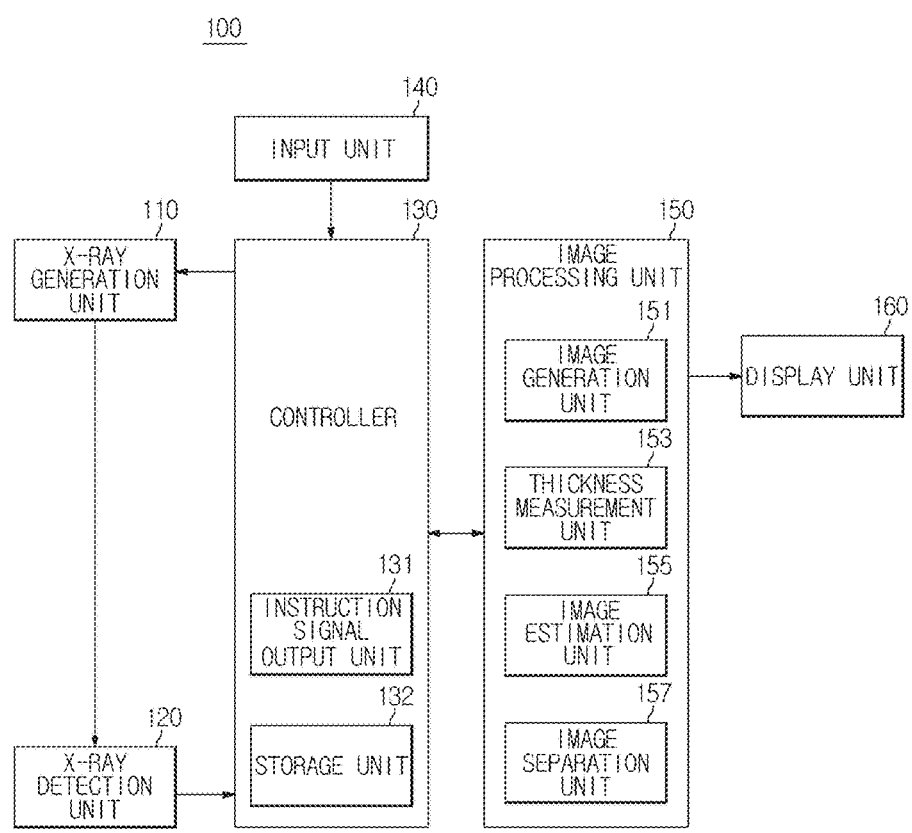
FIG. 2 is a block diagram of a configuration of the X-ray imaging apparatus illustrated in FIG. 1.

FIG. 2 is a block diagram of the configuration of the X-ray imaging apparatus 100 of FIG. 1.

Referring to FIG. 2, the X-ray imaging apparatus 100 of FIG. 1 may include an X-ray generation unit 110, an X-ray detection unit 120, a controller 130, an image processing unit 150, an input unit 140, and a display unit 160.

The X-ray generation unit 110 is configured to generate X-rays and to radiate the X-rays onto the object ob. The X-ray generation unit 110 may generate the X-rays using power supplied by a power supply unit (not shown), energy of the X-rays may be controlled by a tube voltage, and an intensity or a radiation dose of the X-rays may be controlled by a tube current and an X-ray exposure time.

Also, in the present embodiment, the X-ray generation unit 110 may radiate both low energy X-rays $E_L$ and high energy X-rays $E_H$; however, basically, the X-ray generation unit 110 may radiate single energy X-rays. In detail, in the present embodiment, both the low energy X-rays $E_L$ and the high energy X-rays $E_H$ are radiated only when a first mask image and a second mask image of the object ob used to measure the thickness of the object ob are obtained, and in other cases, the single energy X-rays are radiated. Hereinafter, for convenience of explanation, the single energy X-rays basically radiated in the present embodiment are the low energy X-rays $E_L$.

The X-ray generation unit 110 may radiate monochromatic or polychromatic X-rays. The X-ray generation unit 110 may include an X-ray tube 111 that generates the X-rays.

Figure 3:
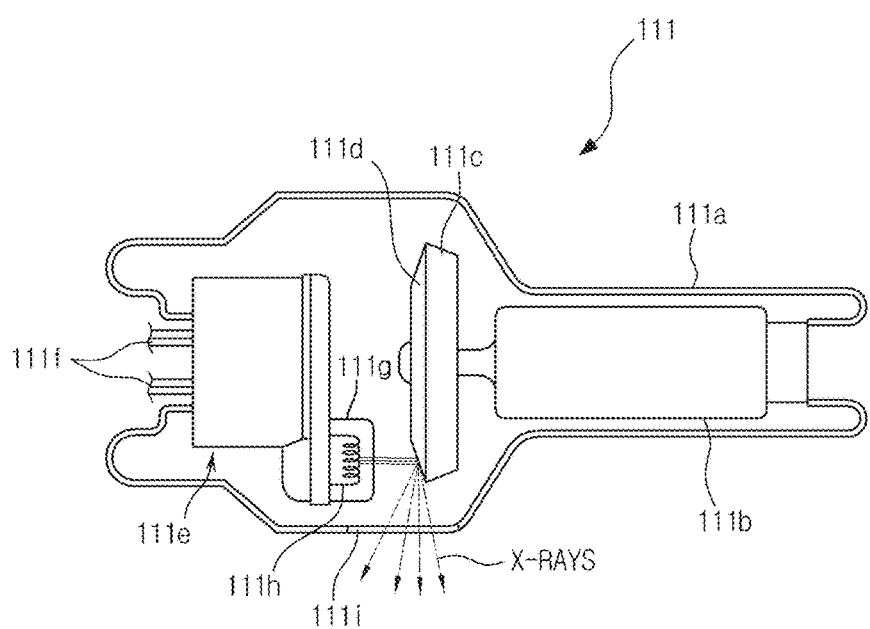
FIG. 3 illustrates a structure of an X-ray tube.

FIG. 3 illustrates the structure of the X-ray tube 111.

Referring to FIG. 3, the X-ray tube 111 may be implemented with a two-pole vacuum tube including an anode 111c and a cathode 111e, wherein a tube body may be a glass bulb 111a formed of silicic acid hard glass.

The cathode 111e includes a filament 111h and a focusing electrode 111g that focuses electrons. The focusing electrode 111g is also referred to as a focusing cup. The inside of the glass bulb 111a is in a high vacuum state of about 10 mmHg, and the cathode filament 111h is heated to a high temperature, thereby generating thermoelectrons. In this case, the filament 111h may be a tungsten (W) filament; however, embodiments of the present invention are not limited thereto. Also, the above-described thermoelectrons may be generated by applying currents to electrical conducting wires 111f connected to the filament 111h. In FIG. 3, the filament 111h is used in the cathode 111e. However, this is merely an embodiment, and carbon nanotubes that may be driven with a high speed pulse may also be used in the cathode 111e.

The anode 111c may be mainly formed of copper (Cu), and a target material 111d may be formed at a side facing the cathode 111e. Here, the target material 111d may be a high resistance material, such as chromium (Cr), iron (Fe), cobalt (Co), nickel (Ni), tungsten (W), and molybdenum (Mo). However, embodiments of the present invention are not limited thereto. In this case, the higher the melting point of the target material 111d, the smaller a focal spot size.

When a high voltage is applied between the cathode 111e and the anode 111c, the thermoelectrons generated in the filament 111h are accelerated, collide with the target material 111d of the anode 111c, and thus generate X-rays. The generated X-rays may be radiated to the outside through a window 111i. In this case, the window 111i may be a beryllium (Be) thin film; however, embodiments of the present invention are not limited thereto.

Also, the target material 111d may be rotated by a rotor 111b. When the target material 111d is rotated, thermal accumulation may be increased by 10 times or more per unit area, and the focal spot size may be reduced compared to the case in which the target material 111d is fixed.

A voltage applied between the cathode 111e and the anode 111c of the X-ray tube 111 is referred to as a tube voltage, and the size of the tube voltage may be indicated by a peak value kVp. When the tube voltage increases, emission acceleration of the thermoelectrons increases. As a result, the energy (photon energy) of the X-rays generated while colliding with the target material 111d may be increased. In this case, the tube voltage may be generally 70 to 120 kVp; however, embodiments of the present invention are not limited thereto.

Also, a current that flows through the X-ray tube 111 is referred to as a tube current. The tube current may be indicated by an average value mA. When the tube current increases, the radiation dose (the number of X-ray photons) of the X-rays may be increased.

Thus, energy levels of the X-rays may be adjusted by adjusting the tube voltage, and strengths and radiation doses of the X-rays may be adjusted by adjusting the tube current and the X-ray exposure time. Thus, the energy levels or strengths of the radiated X-rays may be adjusted by adjusting the tube voltage or the tube current according to the type or characteristics of the object ob.

The X-ray generation unit 110 generates the X-rays using the above-described X-ray tube 111 and radiates the generated X-rays onto the object ob.

When the X-rays are radiated onto the object ob by the X-ray generation unit 110, a degree of X-ray attenuation may vary according to a material inside the object ob and energy levels of the radiated X-rays. Here, a numerical expression of the degree of X-ray attenuation is referred to as an attenuation coefficient. This will now be described with reference to FIG. 4.

Figure 4:
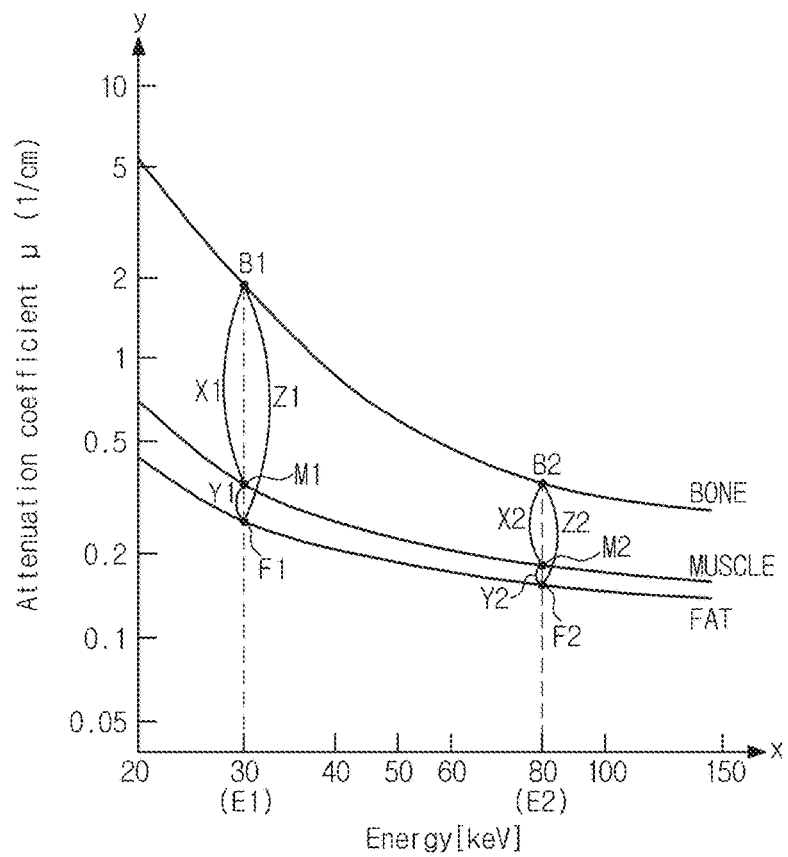
FIG. 4 is a graph showing the relationship between X-ray energy and an attenuation coefficient according to each of materials inside an object.

FIG. 4 is a graph showing the relationship between the energy level of the X-rays and the attenuation coefficient according to each of materials inside the object ob. The x axis represents photon energy radiated onto the object ob, and the y axis represents the attenuation coefficient.

As shown in FIG. 4, a curve indicating an attenuation coefficient of a bone is located above a curve indicating an attenuation coefficient of a soft tissue (muscle and fat). In detail, when X-rays at the same energy level, for example, E1, are radiated, an attenuation coefficient B1 of the bone is larger than an attenuation coefficient M1 of the muscle, and the attenuation coefficient M1 of the muscle is larger than an attenuation coefficient F1 of the fat. That is, the materials inside the object ob have different attenuation coefficients, and the harder the material, the larger the attenuation coefficient of the material.

As shown in FIG. 4, when X-rays having an energy level E1 and an energy level E2 are radiated onto the bone that is the material inside the object ob, the attenuation coefficient B1 of the bone at the relatively low energy level E1 is larger than an attenuation coefficient B2 of the bone at the relatively high energy level E2. Similarly, even in the muscle or the fat, the attenuation coefficient M1 or F1 when the energy level of the X-rays is E1 is larger than an attenuation coefficient M2 or F2 when the energy level of the X-rays is E2. That is, the lower the energy level of the X-rays radiated onto the object ob, the larger the attenuation coefficient.

The attenuation coefficient may be obtained using Equation 1 below:

$$I = I_0 \cdot e^{-\mu(E) \cdot T}$$ [Equation 1]

Here, $I_0$ is a intensity of X-rays radiated onto a material, I is a intensity of the X-rays transmitted by the material, $\mu(E)$ is an attenuation coefficient of the material with respect to the X-rays having an energy level E, and T is a thickness of the material through which the X-rays are transmitted.

According to Equation 1, the larger the attenuation coefficient, i.e., the harder the material or the lower the energy level of the radiated X-rays, and the thicker the material, the lower the intensity of the transmitted X-rays.

As described above, as the energy level of the X-rays radiated onto the object ob varies, the attenuation coefficient of each of the materials inside the object ob varies. Here, varying the attenuation coefficient will be understood as varying the transmittance of the X-rays.

In this way, since the X-ray transmittance with respect to each of the materials inside the object ob varies as the energy level of the X-rays radiated onto the object ob varies, an X-ray image having an improved contrast ratio with respect to each of the materials inside the object ob may be obtained. In detail, a plurality of X-rays having different energy levels are radiated, an X-ray image corresponding to each type of X-rays is obtained, and then the X-ray image in which the materials inside the object ob are separated or in which a certain material appears clearer than the other materials may be obtained using the obtained X-ray images.

Figure 5A:
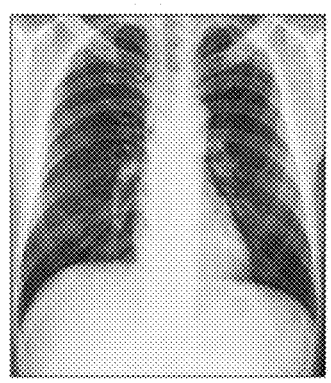
FIGS. 5A through 5D are images obtained according to X-ray energy and differential images subtracted from the images.
Figure 5B:
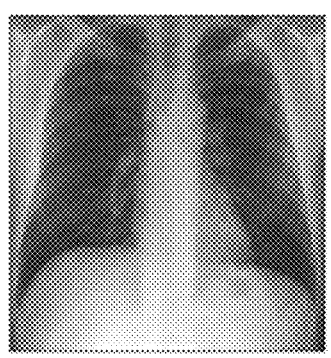
Figure 5C:
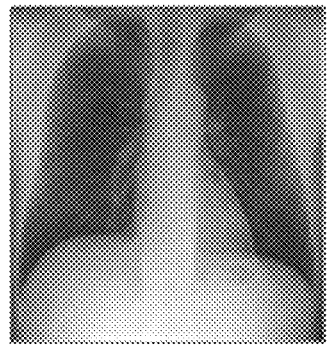
Figure 5D:
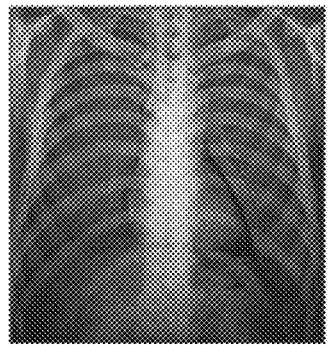

That is, referring to FIG. 5, when the object ob is the breast of a human being, an image obtained by radiating X-rays having a low energy level onto the object ob is shown in FIG. 5A, and an image obtained by radiating X-rays having a high energy level onto the object ob is shown in FIG. 5B. Comparing FIG. 5A with FIG. 5B, there is a difference in brightness between bones and soft tissues. Also, when dual-energy X-ray absorptiometry is applied to the image of FIG. 5A and the image of FIG. 5B, an image in which only the soft tissues are separated, as shown in FIG. 5C, or an image in which only the bones are separated, as shown in FIG. 5D, may be obtained.

For example, an image in which the bones are removed and the soft tissues appear clear may be obtained by multiplying the image of FIG. 5A by a predetermined weighted value and then subtracting the weighted value from the image of FIG. 5B. Conversely, an image in which the soft tissues are removed and the bones appear clear may be obtained by multiplying the image of FIG. 5B by a predetermined weighted value and then subtracting the weighted value from the image of FIG. 5A. However, embodiments of the present invention are not limited thereto.

Meanwhile, in order to obtain an X-ray image of a dynamic organ, such as blood vessels, photographing is required a plurality of times. Thus, generally, a user sets a photographing period using the input unit 140 and radiates X-rays onto the object ob according to the set photographing period, thereby generating an X-ray image indicating a change of the object ob over time.

In this case, energy levels of the X-rays radiated so as to obtain a blood vessel X-ray image may be different. This is because an attenuation coefficient of iodine that is a component of a contrast medium varies according to the energy level of the radiated X-rays and thus an image of the blood vessels may be easily separated from the X-ray image.

To this end, X-rays having different energy levels may be sequentially radiated onto the object ob at a predetermined period. In order to reduce the occurrence of errors caused by an radiation time difference of the sequentially radiated X-rays, the X-rays may be non-uniformly radiated. That is, intervals at which a plurality of types of X-rays are radiated need not be the same.

Figure 6:
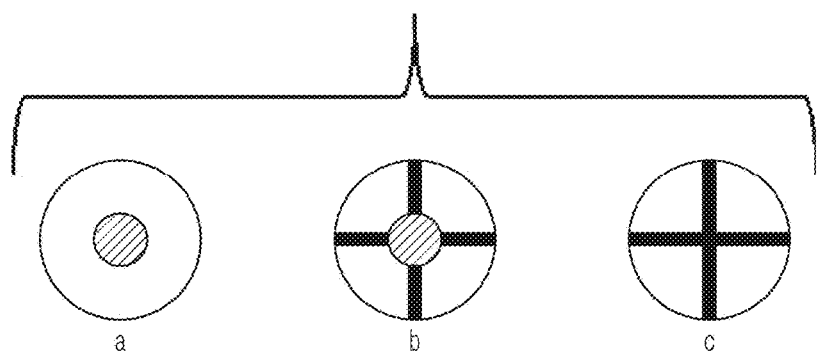
FIG. 6 is a conceptual view schematically illustrating a mask image, a live image, and a differential image.
Figure 7:
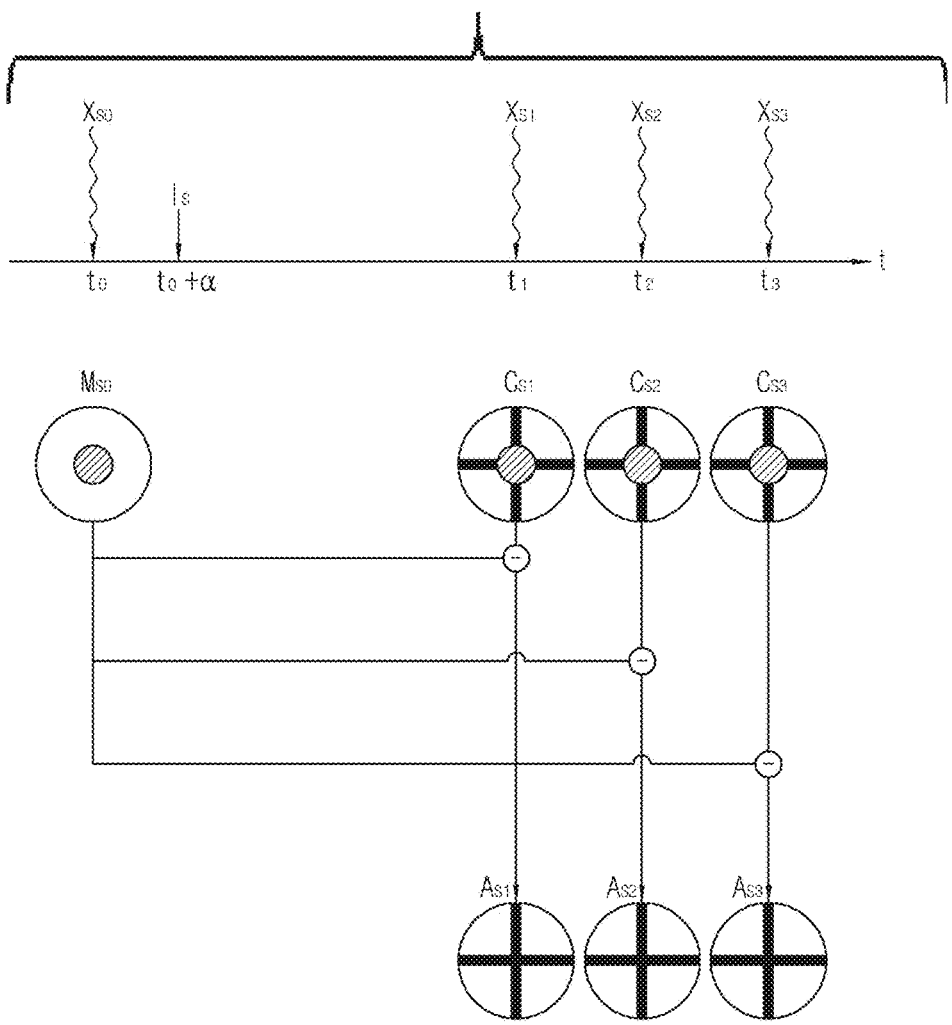
FIG. 7 is a conceptual view illustrating an example in which a digital subtraction X-ray image is obtained.
Figure 8:
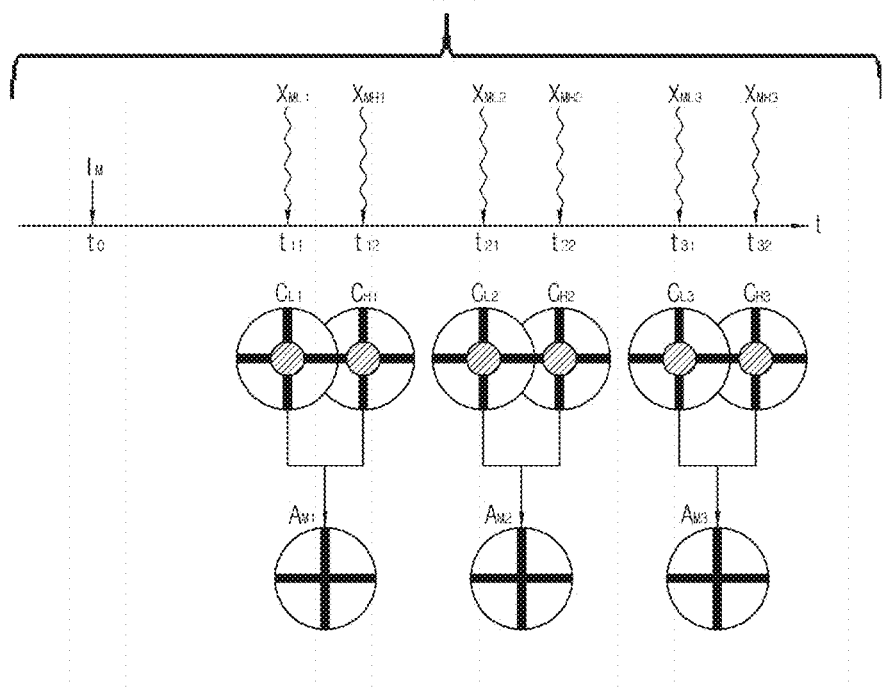
FIG. 8 is a conceptual view illustrating another example in which a digital subtraction X-ray image is obtained.

FIG. 6 is a conceptual view schematically illustrating a mask image, a live image, and a differential image obtained by subtracting the mask image from the live image, FIG. 7 is a conceptual view illustrating an example in which a digital subtraction X-ray image is obtained, and FIG. 8 is a conceptual view illustrating another example in which a digital subtraction X-ray image is obtained.

In FIG. 6, a is a mask image. The mask image is an X-ray image obtained by radiating X-rays onto the object ob before the contrast medium is injected into the object ob. b is a live image. The live image is an X-ray image obtained by radiating X-rays onto the object ob after the contrast medium is injected into the object ob. c is a differential image obtained by subtracting the mask image from the live image, i.e., a digital subtraction angiography (DSA) image. The DSA image is an X-ray image in which blood vessels appear clear and materials other than the blood vessels into which the contrast medium is injected, for example, the bones and the soft tissues, are removed.

Generally, the blood vessels cannot be seen through simple X-ray photographing. Thus, the contrast medium is injected into the blood vessels, and X-rays are radiated onto the object ob, thereby checking the shape of the blood vessels into which the contrast medium is injected. This method is referred to as angiography.

In this case, there are several methods of obtaining a DSA image. A method of obtaining a DSA image by radiating single energy X-rays and a method of obtaining a DSA image by radiating dual energy X-rays among them may be mainly used.

FIG. 7 is a conceptual view illustrating a method of obtaining a DSA image by radiating single energy X-rays. In FIG. 7, $X_{S0}$, $X_{S1}$, $X_{S2}$, and $X_{S3}$ are single energy X-rays, radiation times of which are $t_0$, $t_1$, $t_2$, and $t_3$. $I_S$ is a contrast medium injected into the object ob at a time $(t_0+\alpha)$. Also, $M_{S0}$ is a mask image obtained at a time $t_0$, and $C_{S1}$, $C_{S2}$, and $C_{S3}$ are single energy live images obtained at times $t_1$, $t_2$, and $t_3$ after the contrast medium is injected into the object ob. Also, $A_{S1}$, $A_{S2}$, and $A_{S3}$ are DSA images extracted at the times $t_1$, $t_2$, and $t_3$ after the contrast medium is injected into the object ob.

Referring to FIG. 7, in order to firstly capture the mask image that is an image before the contrast medium is injected into the object ob, single energy X-rays $X_{S0}$ are radiated at the time $t_0$. The mask image $M_{S0}$ may be obtained from the radiated X-rays $X_{S0}$. The contrast medium $I_S$ is injected into the object ob at the time $(t_0+\alpha)$ at which a predetermined amount of time elapses from the time $t_0$ at which the mask image $M_{S0}$ is obtained. In order to obtain a blood vessel image, after a sufficient time at which the contrast medium $I_S$ is diffused along the blood vessels elapses, single energy X-rays $X_{S1}$ are radiated at the desired time $t_1$. The live image $C_{S1}$ may be obtained from the singe energy X-rays $X_{S1}$ radiated in this way after the contrast medium $I_S$ is injected at the time $t_1$. Finally, by subtracting the mask image $M_{S0}$ from the live image $C_{S1}$ after the contrast medium $I_S$ is injected into the object ob, the DSA image $A_{S1}$ may be obtained at the time $t_1$.

In DSA, there is a time difference between acquisition times of two images, i.e., the mask image and the live image. As mentioned above, the time difference occurs because the X-ray image is obtained after a sufficient time for the contrast medium to become diffused into the blood vessels to some degrees elapses. For example, there is a time difference between the acquisition time $t_0$ of the mask image $M_{S0}$ and the acquisition time $t_1$ of the live image $C_{S1}$, as illustrated in FIG. 7.

The time difference may cause an error in the DSA image obtained by subtracting the mask image from the live image. This is because, when the object ob is moved during diffusion of the contrast medium, geometric deformation may occur in the X-ray image, or the movement of the object ob, such as contraction or expansion, may cause an error when a blood vessel region is extracted.

Angiography based on multiple energy X-rays may be used to reduce this error. FIG. 8 is a conceptual view illustrating angiography based on the multiple energy X-rays. Referring to FIG. 8, unlike in angiography based on single energy X-rays, X-rays having different energy levels are sequentially radiated onto the object ob. In this case, the X-rays having different energy levels will be referred to as low energy X-rays and high energy X-rays. Here, a low energy level and a high energy level have relative meanings and may vary according to the object ob.

In FIG. 8, $X_{ML1}$, $X_{ML2}$, and $X_{ML3}$ are low energy X-rays, irradiation times of which are $t_{11}$, $t_{21}$, and $t_{31}$, and $X_{MH1}$, $X_{MH2}$, and $X_{MH3}$ are high energy X-rays, irradiation times of which are $t_{12}$, $t_{22}$, and $t_{32}$. $I_M$ is a contrast medium injected into the object ob at a time $t_0$. Also, $C_{L1}$, $C_{L2}$, and $C_{L3}$ are low energy live images obtained at the times $t_{11}$, $t_{21}$, and $t_{31}$ after the contrast medium is injected into the object ob, and $C_{H1}$, $C_{H2}$, and $C_{H3}$ are high energy live images obtained at the times $t_{12}$, $t_{22}$, and $t_{32}$ after the contrast medium is injected into the object ob. Also, $A_{M1}$, $A_{M2}$, and $A_{M3}$ are DSA images obtained at the times $t_{12}$, $t_{22}$, and $t_{32}$ after the contrast medium is injected into the object ob.

Referring to FIG. 8, before X-rays are radiated, the contrast medium $I_M$ is injected into the object ob. After the contrast medium $I_M$ is injected into the object ob, a sufficient time for the contrast medium $I_M$ to become diffused throughout the blood vessels is required so as to obtain a blood vessel image.

After the sufficient time for the contrast medium $I_M$ to become diffused into the blood vessels elapses, two types of X-rays having different energy levels are sequentially radiated. In detail, low energy X-rays $X_{ML1}$ and high energy X-rays $X_{MH1}$ are radiated at the times $t_{11}$ and $t_{12}$ that are times after the sufficient time for the contrast medium $I_M$ to become diffused into the blood vessels elapses.

When two types of materials are to be separated in an X-ray image, the materials to be separated need to have different X-ray attenuation characteristics, and X-ray images corresponding to different energy bands need to be obtained. To this end, an image generation unit 151 may generate X-ray images corresponding to different energy levels. For example, as illustrated in FIG. 8, corresponding to the low energy X-rays $X_{ML1}$ and the high energy X-rays $X_{MH1}$, the image generation unit 151 may generate a low energy live image $C_{L1}$ and a high energy live image $C_{H1}$ sequentially after the contrast medium $I_M$ is injected into the object ob.

In the X-ray images $C_{L1}$ and $C_{H1}$ generated in this way, there is a difference in brightness between the blood vessels (contrast medium), the bones, and the soft tissues that are materials to be separated inside the object ob. This is because, as described above, attenuation characteristics of the materials depend on energy levels of X-rays.

Two material images may be separated in the X-ray image by performing an arithmetic operation of multiplying at least one of the two X-ray images $C_{L1}$ and $C_{H1}$ by a predetermined weighted value and then subtracting the weighted value from the other X-ray image twice. This is referred to as dual-energy X-ray absorptiometry.

In angiography based on multiple energy X-rays, a difference between an acquisition time of a low energy live image and an acquisition time of a high energy live image is smaller than a difference between an acquisition time of a mask image and an acquisition time of a live image in angiography based on single energy X-rays. Thus, by applying angiography based on multiple energy X-rays, a time in which the movement of the object ob may occur is reduced. As a result, DSA image errors that may occur due to the movement of the object ob may be reduced.

In this way, in the related art, when the DSA image is obtained, a motion artifact may occur in the DSA image due to the movement of the object ob. Thus, in the present embodiment, in order to solve this problem, thickness information of the object ob is measured using a mask image and a phantom image obtained before a contrast medium is injected into the object ob, and a live image is estimated from the object ob after the contrast medium is injected into the object ob based on a reference phantom image in which the measured thickness information is indicated, thereby obtaining a clear DSA image having no motion artifact even when the object ob is moved. Hereinafter, this will be described in detail.

Referring back to FIG. 2, the X-ray detection unit 120 may detect the X-rays transmitted by the object ob, may convert the detected X-rays into electrical signals and may obtain X-ray data. Also, the X-ray detection unit 120 may provide the obtained X-ray data to the image processing unit 150.

In general, the X-ray detection unit 120 may be classified according to a material composition method, a method of converting detected X-rays into electrical signals, and a method of obtaining X-ray data. Hereinafter, various methods of detecting X-rays, converting the detected X-rays into electrical signals and obtaining X-ray data using the X-ray detection unit 120 will be described.

First, the X-ray detection unit 120 is classified as a single type device or a combined type device according to the material composition method.

When the X-ray detection unit 120 is configured as the single type device, a part for detecting X-rays and generating electrical signals and a part for reading and processing the electrical signals may be formed as a semiconductor of a single material or may be manufactured in a single process, such as when a charge coupled device (CCD) that is a light receiving device or a complementary metal oxide semiconductor (CMOS) is used as the X-ray detection unit 120.

When the X-ray detection unit 120 is configured as the combined type device, a part for detecting X-rays and generating electrical signals and a part for reading and processing the electrical signals may be formed of different materials or may be manufactured in different processes, such as when X-rays are detected using a light receiving device such as a photodiode, a CCD, or cadmium zinc telluride (CdZnTe) and the electrical signals are read and processed using a complementary metal oxide semiconductor read out integrated circuit (CMOS ROIC), when the X-rays are detected using a strip detection unit and the electrical signals are read and processed using the CMOS ROIC, and when an a-Si or a-Se flat panel system is used as the X-ray detection unit 120.

The X-ray detection unit 120 may be classified as a direct conversion type or an indirect conversion type according to a method of converting X-rays into electrical signals.

In the direct conversion method, electrons and holes that are temporarily generated in a light receiving device due to radiated X-rays and that are moved to an anode and a cathode due to an electric field applied to both ends of the light receiving device are converted into electrical signals. In the direct conversion method, a-Se, CdZnTe, $HgI_2$, $PbI_2$, or the like may be used as the light receiving device; however, embodiments of the present invention are not limited thereto.

In the indirect conversion method, a scintillator is provided between a light receiving device and an X-ray generation unit, the light receiving device detects photons having a wavelength in a visible light region as X-rays radiated by the X-ray generation unit react with the scintillator, and the detected photons are converted into electrical signals. In the indirect conversion method, a-Si may be used as the light receiving device; however, embodiments of the present invention are not limited thereto. Also, a gadolinium oxysulfide (GADOX) scintillator having a thin film shape or a micro pillar-shaped or needle-shaped CSI(TI) scintillator may be used; however, embodiments of the present invention are not limited thereto.

Also, the X-ray detection unit 120 may be classified according to a method of obtaining X-ray data through a charge integration mode in which charges are stored for a predetermined amount of time and then signals are obtained from the charges or a photon counting mode in which photons having threshold energy or more are counted whenever a signal is generated from single X-ray photons.

The image processing unit 150 may include an image generation unit 151, a thickness measurement unit 153, an image estimation unit 155, and an image separation unit 157, as illustrated in FIG. 2.

The image generation unit 151 may generate an X-ray image based on the X-ray data provided from the X-ray detection unit 120. In detail, as illustrated in FIG. 7, when the single energy X-rays $X_{S0}$ are radiated onto the object ob at the time $t_0$, the X-ray detection unit 120 may detect X-ray data regarding the single energy X-rays $X_{S0}$ that transmitted by the object ob, and the image generation unit 151 may generate the mask image $M_{S0}$ based on the detected X-ray data. Similarly, after the contrast medium $I_S$ is injected into the object ob, the live images $C_{S1}$, $C_{S2}$, and $C_{S3}$ regarding the single energy X-rays $X_{S1}$, $X_{S2}$, $X_{S3}$ radiated at the times $t_1$, $t_2$, and $t_3$ may be generated.

Also, the image generation unit 151 in accordance with the present embodiment may generate a phantom image together with the above-described mask image in order to measure thickness information of the object ob. Here, a phantom is a model of the object ob that is formed of the same material as a material used to form the object ob and that may represent both the thickness of the object ob and a mixture ratio of the material, as illustrated in FIGS. 9A through 9C.

Explaining a phantom 40 with reference to FIGS. 9A through 9C, for example, when the object ob is breast fat, the object ob may include two materials including adipose tissue $T_1$ (hereinafter referred to as a first material) and glandular tissue $T_2$ (hereinafter referred to as a second material). Assuming that the object ob has a minimum thickness of $D_1$ and a maximum thickness of $D_2$ according to its position, the phantom 40 illustrated in FIGS. 9A through 9C may be manufactured.

In detail, the phantom 40 may be manufactured to include a rectangular front surface $S_1$ and rear surface $S_2$ parallel to a plane formed by the x-axis and the y-axis and a right-trapezoidal left surface $S_3$ and right surface $S_4$ parallel to a plane formed by the y-axis and the z-axis, to have a thickness $D_1$ in the y-axis direction at the front surface $S_1$, a thickness that linearly increases toward the rear surface $S_2$ and a thickness $D_2$ in the y-axis direction at the rear surface $S_2$.

Here, since the first material $T_1$ and the second material $T_2$ are coupled to each other in a diagonal line, a mixture ratio of the first material $T_1$ and the second material $T_2$ may be changed from the left surface $S_3$ to the right surface $S_4$. That is, although the mixture ratio of the first material $T_1$ and the second material $T_2$ is 1:0 in the y-axis direction at the left surface $S_3$ of the phantom 40, the ratio of the first material $T_1$ linearly decreases toward the right surface $S_4$, whereas the ratio of the second material $T_2$ linearly increases, and the mixture ratio of the first material $T_1$ and the second material $T_2$ in the y-axis direction at the right surface $S_4$ may be 0:1.

The phantom 40 formed in this way may represent all of the material, the thickness, and the mixture ratio of the object ob assumed above. However, the shape of the phantom 40 is not limited to the above-described examples, and any other type of phantom that may be a model of the object ob may also be used.

Figure 11A:
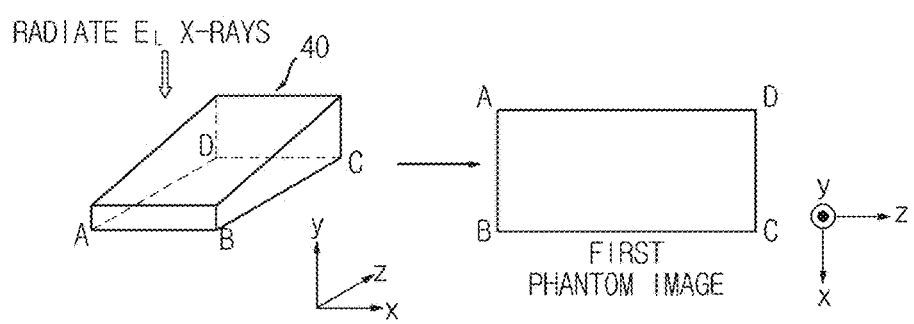
FIGS. 11A and 11B illustrate an operation of generating a phantom image.
Figure 11B:
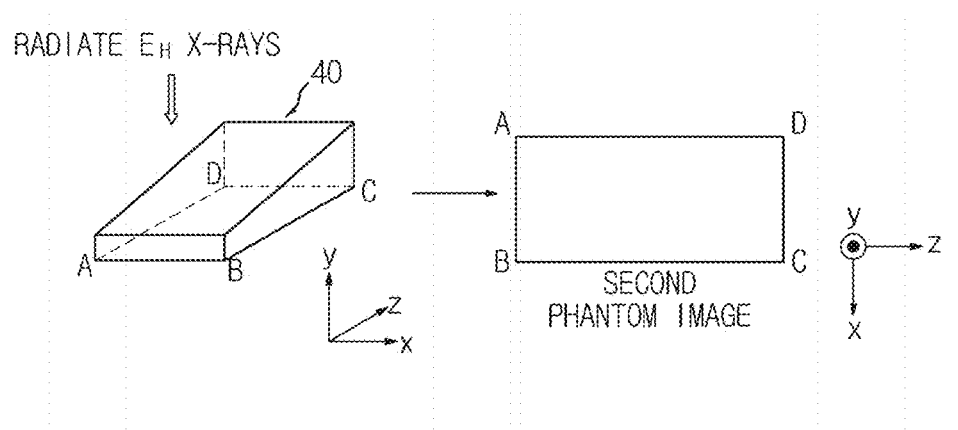

When X-rays are radiated onto the phantom 40, each of the low energy X-rays $E_L$ and the high energy X-rays $E_H$ may be radiated only once. That is, as illustrated in FIGS. 11A and 11B, each of the low energy X-rays $E_L$ and the high energy X-rays $E_H$ may be radiated onto the phantom 40, the X-ray detection unit 120 in accordance with the present embodiment may detect the low energy X-rays $E_L$ and the high energy X-rays $E_H$ transmitted by the phantom 40, and the image generation unit 151 may generate a first phantom image and a second phantom image that correspond to the low energy X-rays $E_L$ and the high energy X-rays $E_H$ that are transmitted by the phantom 40 and detected by the X-ray detection unit 120.

The first phantom image and the second phantom image that are images of X-rays transmitted by the phantom 40 are generated in this way because the phantom 40 is a model having the same thickness as the object ob, as described above. In other words, even when the object ob is moved, the thickness of the object ob is not changed and a motion artifact that occurs in the DSA image due to the movement of the object ob is removed.

In this case, in order to obtain thickness information of each pixel of the mask image on the object ob, low energy X-rays and high energy X-rays need to be radiated onto the object twice. Hereinafter, for convenience of explanation, a mask image obtained by radiating the low energy X-rays will be referred to as a first mask image, and a mask image obtained by radiating the high energy X-rays will be referred to as a second mask image. Similarly, a phantom image obtained by radiating the low energy X-rays will be referred to as a first phantom image, and a phantom image obtained by radiating the high energy X-rays will be referred to as a second phantom image.

Also, in the present embodiment, basically, single energy X-rays are radiated except for the case in which X-rays are radiated for thickness measurement, and although the radiated X-rays will be explained as low energy X-rays for convenience of explanation, embodiments of the present invention are not limited thereto, and high energy X-rays may also be used.

Thus, a live image obtained by radiating the low energy X-rays will be referred to as a first live image, and a live image obtained by radiating the high energy X-rays estimated by the image estimation unit 155 will be referred to as a second live image.

FIG. 10 illustrates an operation of generating a mask image, and FIGS. 11A and 11B illustrate an operation of generating a phantom image.

In FIG. 10, the X-ray generation unit 110 radiates the low energy X-rays $E_L$ in the y-axis direction, more precisely, in a direction in which a y value decreases, from an upper part of the object ob n times (n≥2) at time intervals of $t_1, t_2, \ldots,$ and $t_{n-1}$, and the X-ray detection unit 120 detects the low energy X-rays $E_L$ transmitted by the object ob n times.

The image generation unit 151 may generate a first mask image based on firstly detected X-rays, a second first mask image based on secondly detected X-rays, and a third first mask image based on thirdly detected X-rays. The image generation unit 151 may generate n first mask images corresponding to the number of times X-rays are detected in this way.

In this case, the intensity of the detected X-rays may be understood as a pixel value of the first mask image.

In FIG. 11A, the X-ray generation unit 110 radiates the low energy X-rays $E_L$ in the direction in which the y-value decreases, from an upper part of the phantom 40, and the X-ray detection unit 120 detects the low energy X-rays $E_L$ that transmit the phantom 40.

The image generation unit 151 generates a first phantom image having a rectangular shape from the detected low energy X-rays $E_L$. Similarly, the strength of the detected X-rays may be understood as a pixel value of the first phantom image.

In FIG. 11B, only an energy level of the X-rays radiated by the X-ray generation unit 110 in FIG. 11A is changed. That is, the X-ray generation unit 110 radiates the high energy X-rays $E_H$ in the direction in which the y value decreases from the upper part of the phantom 40 once, and the X-ray detection unit 120 detects the high energy X-rays $E_H$ transmitted by the phantom 40.

Thus, the image generation unit 151 generates a second phantom image having the same shape as the first phantom image generated in FIG. 11A but having a different pixel value from the first phantom image generated in FIG. 11A.

In this way, the image generation unit 151 may generate a plurality of first mask images corresponding to the number of times X-rays are radiated and energy levels of the radiated X-rays and first and second phantom images.

The thickness measurement unit 153 may measure the thickness information of the object ob.

A method of measuring the thickness information of the object ob may include a method using calibration, whereby the thickness information of the object ob and the mixture ratio of the material used to form the object ob are estimated from an X-ray image, a method using a distance between compression pads, and a method using a computed tomography (CT) image; however, embodiments of the present invention are not limited thereto.

Firstly, the method using calibration will be described with reference to FIGS. 12 and 13.

Figure 12A:
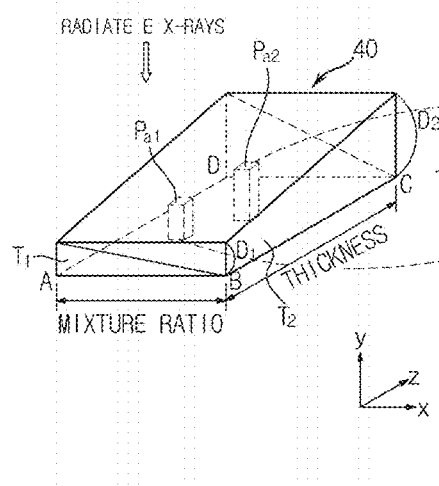
FIGS. 12A and 12B illustrate the relationship between a phantom and a phantom image.
Figure 12B:
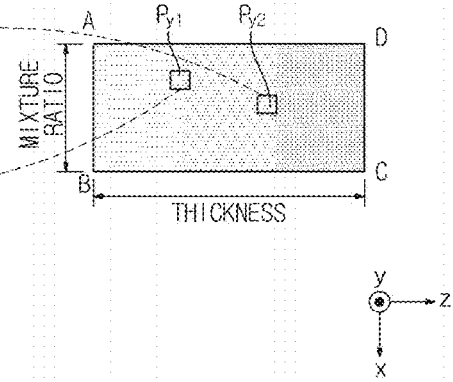
Figure 13:
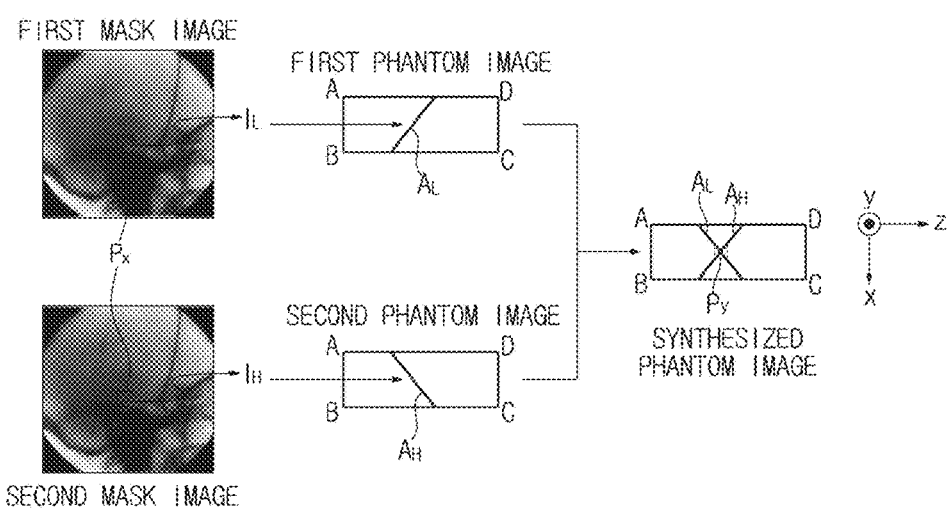
FIG. 13 illustrates an operation of performing calibration.

FIGS. 12A and 12B illustrate the relationship between a phantom and a phantom image, and FIG. 13 schematically illustrates an operation of performing calibration.

A phantom 40 of FIG. 12A is the same as the phantom 40 of FIGS. 9A through 9C. A phantom image of FIG. 12B is a phantom image generated from the upper part of the phantom 40 by radiating X-rays, as illustrated in FIGS. 11A and 11B and may be any one of the first phantom image and the second phantom image. That is, the phantom image of FIG. 12B may correspond to any one of the low energy X-rays $E_L$ and the high energy X-rays $E_H$.

Since the phantom image is generated based on the X-rays transmitted by the phantom 40, there is a pixel of the phantom image corresponding to each part of the phantom 40. Thus, as illustrated in FIGS. 12A and 12B, a pixel of the phantom image corresponding to a part $Pa_1$ of the phantom 40 will be referred to as $Py_1$, and a pixel of the phantom image corresponding to a part $Pa_2$ of the phantom 40 will be referred to as $Py_2$.

Thus, $Py_1$ includes information regarding the thickness of $Pa_1$ and the mixture ratio of a material used to form $Pa_1$, and $Py_2$ includes information regarding the thickness of $Pa_2$ and the mixture ratio of a material used to form $Pa_2$. For example, if $Pa_1$ of the phantom 40 has a thickness of 5.5 cm and a mixture ratio of 7:3 between the first material $T_1$ and the second material $T_2$, the pixel $Py_1$ corresponding to $Pa_1$ may include information of 'the thickness of 5.5 cm and the mixture ratio of 7:3 between the first material $T_1$ and the second material $T_2$.'

Similarly, if $Pa_2$ of the phantom 40 has a thickness of 7.5 cm and a mixture ratio of 5:5 between the first material $T_1$ and the second material $T_2$, the pixel $Py_2$ corresponding to $Pa_2$ may include information of 'the thickness of 7.5 cm and the mixture ratio of 5:5 between the first material $T_1$ and the second material $T_2$.'

In this way, each pixel of the phantom image includes information of the thickness of a part of the phantom 40 and the material used to form the part of the phantom 40.

Since the phantom 40 is a model of the object ob, there may be a part of the phantom 40 corresponding to each part of the object ob.

Consequently, there is a pixel of the phantom image corresponding to each part of the object ob, and information regarding the thickness of the pixel and the mixture ratio of the material used to form the pixel is information regarding a part of the object ob corresponding to the pixel.

Thus, the pixel of the phantom image corresponding to each part of the object ob is detected so that the thickness of the part of the object ob and the mixture ratio of the material used to form the part of the object ob may be known. An operation of performing calibration using the thickness of the part of the object ob and the mixture ratio of the material used to form the part of the object ob is illustrated in FIGS. 12A and 12B.

That is, a first mask image among a plurality of first mask images generated by the image generation unit 151 may be set as a first mask image of FIGS. 12A and 12B. Also, an operation of radiating the high energy X-rays $E_H$ may be included in an operation of radiating the low energy X-rays $E_L$ using the X-ray generation unit 110 so as to generate the first mask image so that a second mask image of FIGS. 12A and 12B may be generated.

As described above, in the present embodiment, basically, the X-ray generation unit 110 radiates single energy X-rays onto the object ob, and when calibration is used to measure the thickness of the object ob, dual energy X-rays may be radiated a first time. This is because, when calibration is used to measure the thickness of the object ob, an image of low energy X-rays and an image of high energy X-rays are required.

Thus, the first time, the low energy X-rays and the high energy X-rays are radiated onto the object ob so that a first mask image and a second mask image may be generated.

Referring to FIGS. 12A and 12B, firstly, pixel values of pixels Px at the same position are obtained from the first mask image and the second mask image. In this case, when a pixel value of a pixel Px obtained from the first mask image is referred to as $I_L$ and a pixel value of a pixel Px obtained from the second mask image is referred to as $I_H$, $I_L$ and $I_H$ have different values. This is because, as described above, even in the pixels Px at the same position, an attenuation coefficient varies according to the energy level of radiated X-rays and thus the intensity of the transmitted X-rays also varies.

Pixels (area $A_L$) having the same pixel values as $I_L$ are indicated on a first phantom image, and pixels (area $A_H$) having the same pixel values as $I_H$ are indicated on a second phantom image. Here, since $I_L$ and $I_H$ have different values, gradients of the area $A_L$ and the area $A_H$ may be different.

When the first phantom image and the second phantom image in which the area $A_L$ and the area $A_H$ are indicated are synthesized according to position, a crossing point Py may be detected. That is, the pixel Py of a phantom image (synthesized phantom image) corresponding to the pixel Px of each of the first mask image and the second mask image is obtained.

As described above with reference to FIGS. 11A and 11B, the thickness (and the mixture ratio of the material) information of the pixel Py may be a thickness (and the mixture ratio of the material) of the part of the object ob corresponding to the pixel Px of the object ob.

When this operation is performed in all pixels of the first mask image and the second mask image, thicknesses (and the mixture ratio of the material) of all parts of the object ob may be measured.

A method of measuring the thickness using a compression paddle and a CT image will now be described.

For example, X-rays may be radiated in a state in which upper and lower parts of the object ob are compressed using two compression paddles having a flat panel shape. In this case, a distance between the compression paddles may be the thickness of the object ob.

CT is a procedure, whereby X-rays transmitted by one cross-section of the object ob at several angles while rotating the one cross-section 360° are detected and re-configured and are shown as an image, thereby obtaining an image of the cross-section of the object ob. A length in a vertical direction in the CT image may be the thickness of the object ob.

The thickness measurement unit 153 may display the thickness information of the object ob measured using the above-described method on a first phantom image. An X-ray image if the object ob and the first phantom image in which depth information if a region of interest (ROI) in the X-ray image is displayed are shown in FIGS. 14A and 14B. Hereinafter, the first phantom image in which the thickness information of the object ob is displayed will be referred to as a reference phantom image.

That is, the reference phantom image illustrated in FIG. 14B indicates thickness information of an area $A_1$ of the object ob illustrated in FIG. 14A. When the reference phantom image illustrated in FIG. 14B is the same as the first phantom image generated in FIG. 11A, only the mixture ratio of a material used to form the area $A_1$ varies in the x-axis direction, the thickness of the area $A_1$ is uniform, and the thickness may increase in the z-axis direction (in detail, the thickness may decrease in a direction in which a z value decreases).

The image estimation unit 155 may estimate a second live image by counterplotting the calibration method used to measure the thickness of the object ob using the thickness measurement unit 153 described above.

Figure 15:
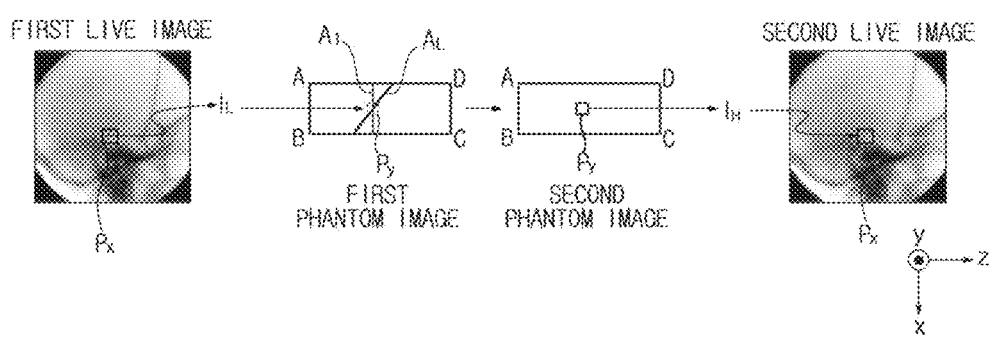
FIG. 15 illustrates an operation of estimating a second live image.

FIG. 15 schematically illustrates an operation of estimating the second live image.

In FIG. 15, assuming that a pixel Px of a first live image obtained by radiating the low energy X-rays after the contrast medium is injected into the object ob has a pixel value of $I_L$, the image estimation unit 155 may detect pixels (area $A_L$) having the same pixel value as $I_L$ from the reference phantom image in which the thickness information (area A1) of the pixel Px of the object ob is displayed.

Next, the image estimation unit 155 may estimate a point Py at which the area $A_1$ and the area $A_L$ cross each other, and may obtain a pixel value of the point Py in the second phantom image. In this case, if the obtained pixel value is $I_H$, the pixel value of the pixel Px in the second live image may also be $I_H$.

When this operation is performed on all pixels of the first live image, all pixel values of the second live image may be estimated. As a result, the second live image that may be obtained when the high energy X-rays $E_H$ are radiated may be estimated without radiating the high energy X-rays $E_H$ onto the object ob.

In the above-described embodiment, the second live image has been estimated from the first live image. However, the second live image may be obtained, and the first live image may be estimated.

Also, images of the object ob corresponding to different energy levels may be consecutively estimated from the estimated second live image. For example, when energy levels of first X-rays, second X-rays, and third X-rays increase sequentially, the image estimation unit 155 may estimate a second X-ray image based on a first X-ray image and may estimate a third X-ray image based on the second X-ray image. An i-th X-ray image in this case may mean an image of the object ob generated by radiating i-th X-rays (where i is 1, 2, and 3).

The image separation unit 157 is configured to generate a final image in which only a blood vessel image is separated, by subtracting the second mask image generated by the image generation unit 151 from the second live image estimated by the image estimation unit 155.

As described above, in order to measure the thickness information of the object ob, the low energy X-rays and the high energy X-rays are sequentially radiated onto the object ob before the contrast medium is injected into the object ob, so that the first mask image and the second mask image may be obtained. Since the first mask image and the second mask image in this case are images before the contrast medium is injected into the object ob, blood vessels do not appear clear in the first mask image and the second mask image.

Also, since the second live image estimated by the image estimation unit 155 is an X-ray image of the object ob estimated after the contrast medium is injected into the object ob, blood vessels appear clearer in the second live image than in the first mask image and the second mask image described above. Thus, comparing the second mask image obtained before the contrast medium is injected into the object ob with the second live image obtained after the contrast medium is injected into the object ob, there is a difference in images of the blood vessels.

Figure 16:
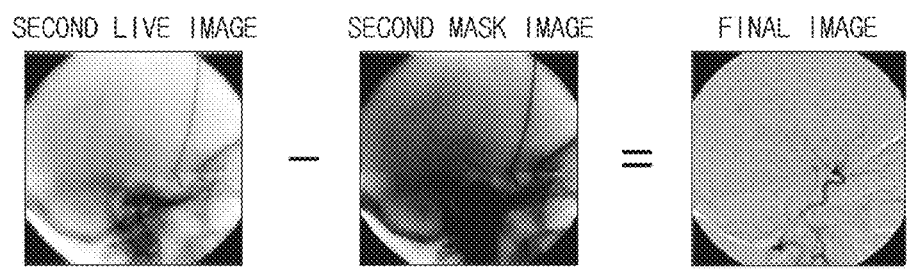
FIG. 16 illustrates an operation of obtaining the second live image estimated in FIG. 15 and a differential image of the second live image.

Thus, the image separation unit 157 may generate a final image in which parts other than the blood vessels are removed and only the blood vessels are indicated by subtracting the second mask image in which the blood vessels do not appear clear from the second live image in which the blood vessels appear clear, as illustrated in FIG. 16.

In this case, the final image may be generated by multiplying the second live image by a predetermined weighted value and then subtracting the second mask image from the second live image. However, embodiments of the present invention are not limited thereto, and the final image may also be generated by multiplying the second mask image by the predetermined weighted value and then subtracting the second live image from the second mask image.

The controller 130 may control the overall operation of the X-ray imaging apparatus 100.

In detail, the controller 130 may include an instruction signal output unit 131 and a storage unit 133.

When a user inputs a diagnosis instruction using the input unit 140 connected to the controller 130 in wired or wireless communication, the instruction signal output unit 131 may output a control instruction signal to radiate X-rays to the X-ray generation unit 110.

In this case, the instruction signal output unit 131 may output the control instruction signal regarding an energy level of the X-rays to be radiated together with the control instruction signal to radiate the X-rays to the X-ray generation unit 110. In detail, the instruction signal output unit 131 may output the control instruction signal regarding an energy value KeV of the X-rays to be radiated, in addition to the control instruction signal regarding low energy X-rays or high energy X-rays to be radiated. The instruction signals may be transmitted at the energy level input by the user using the input unit 140 or an energy level automatically selected according to the part or characteristics of the object ob.

Also, the instruction signal output unit 131 may output a control instruction signal regarding a time interval at which X-rays are to be radiated onto the object ob and the number of times the X-rays are to be radiated onto the object ob, i.e., a control instruction signal regarding the time interval and the number of repetitions. Similarly, the user may transmit the instruction signal at the time interval and with the number of repetitions input by the user using the input unit 140 or may transmit the instruction signal automatically based on previously stored data.

The instruction signal output unit 131 may output control instruction signals to display the first mask image and the second mask image generated by the image processing unit 150, the first live image, the second live image, and the DSA image on the display unit 160 to the image processing unit 150.

The storage unit 133 may store data or an algorithm for manipulating the X-ray imaging system 100. For example, compressed data regarding an energy level of X-rays to be radiated according to the part or characteristics of the object ob, a time interval or the number of repetitions of the X-rays radiated onto the object ob, the first phantom image and the second phantom image, the first mask image and the second mask image, the first live image and the second live image, the reference phantom image, and the DSA image may be stored in the storage unit 133.

Also, an algorithm for measuring the thickness of the object ob, in particular, an algorithm for applying calibration, and an algorithm for estimating the second live image from the first live image may be stored in the storage unit 133.

The X-ray imaging apparatus 100 in accordance with the present embodiment has been described above. The X-ray imaging apparatus 100 in accordance with the present embodiment measures thickness information of an object ob based on a mask image of the object ob obtained before a contrast medium is injected into the object ob, estimates a live image after the contrast medium is injected into the object ob using a reference phantom image in which the measured thickness information is indicated, and then subtracts the obtained mask image from the estimated live image, thereby generating a final image in which only the blood vessels appear.

In accordance with the present embodiment, the thickness information of the object ob is firstly measured, and the DSA image of the object ob is obtained based on the thickness information, so that, even when the object ob is moved, a motion artifact may be prevented from occurring in the DSA image.

FIG. 17 is a flowchart illustrating a method of controlling an X-ray imaging apparatus in accordance with an embodiment of the present invention.

Firstly, the X-ray generation unit 110 sequentially radiates low energy X-rays and high energy X-rays onto the phantom 40, and the image generation unit 151 generates a first phantom image and a second phantom image based on the low energy X-rays and the high energy X-rays transmitted by the phantom 40 (S1710). Here, the phantom 40 is a model of an object ob in which thickness information of the object ob and information regarding the mixture ratio of a material inside the object ob are the same.

Next, the X-ray generation unit 110 sequentially radiates the low energy X-rays and the high energy X-rays onto the object ob, and the image generation unit 151 generates a first mask image and a second mask image based on the low energy X-rays and the high energy X-rays transmitted by the object ob (S1720).

Next, calibration is performed so as to measure thickness information of the object ob and to generate a reference phantom image in which the measured thickness information is indicated (S1730). Here, an operation of measuring the thickness information of the object ob by performing calibration may be performed by making pixels between the mask image and the phantom image correspond to each other using a pixel value of each of the first phantom image and the second phantom image generated in operation S1710 and the first mask image and the second mask image generated in operation S1720 and by using the thickness information of the object ob of the phantom image. This has already been described above, and thus detailed description thereof will be omitted.

Next, when a contrast medium is injected into the object ob (S1740), the X-ray generation unit 110 radiates low energy X-rays onto the object ob, and the image generation unit 151 generates a first live image corresponding to the low energy X-rays transmitted by the object ob (S1750).

Here, after the contrast medium is injected into the object ob, when the X-ray generation unit 110 radiates X-rays onto the object ob, the X-ray generation unit 110 may radiate the low energy X-rays or the high energy X-rays, as described above.

Next, a pixel value of a predetermined pixel is obtained from the first live image generated by the image estimation unit 15, pixels having the same pixel value are extracted from the reference phantom image in which the thickness information of the object ob is indicated, and then a point that crosses the thickness information is detected from the extracted pixels (S1760).

Next, a pixel value of a pixel corresponding to the crossing point detected in operation S1760 is obtained from the second phantom image, and the obtained pixel value is estimated as a pixel value of a pixel corresponding to the second live image. These operations are repeatedly performed so that a second live image in which all pixel values are estimated may be generated (S1770).

In this case, after the contrast medium is injected into the object ob, as described above, when the X-ray generation unit 110 radiates not the low energy X-rays but the high energy X-rays, the second live image may be generated in operation S1750 described above, and a first live image in which all pixel values are estimated may be generated in operation S1770 described above.

Next, the image separation unit 157 may subtract the second mask image generated in operation S1720 described above from the second live image generated in operation S1770 so that a final image in which all materials other than the blood vessels are removed and only the blood vessels appear may be generated (S1780).

Embodiments of the present invention have been described above. In the above-described embodiments, some elements of the X-ray imaging apparatus 100 may be implemented with a kind of 'module.' Here, the 'module' is a software element or a hardware element, such as a field programmable gate array (FPGA) or an application specific integrated circuit (ASIC), and the module may perform functions. However, the module is not limited to software or hardware. The module may be configured to be in a storage medium that may address the module or to execute one or more processors.

As an example, the module may include elements such as software elements, object-oriented software elements, class elements, and task elements, processes, functions, properties, procedures, subroutines, segments for a program code, drivers, firmware, micro-codes, circuits, data, databases, data structures, tables, arrays, and variables. Functions provided by elements and modules may be combined with a small number of elements and modules or may be subdivided into additional elements and modules. Furthermore, the elements and modules may execute one or more central processing units (CPUs) within a device.

Some embodiments of the present invention may be embodied through a medium including a computer-readable code/command for controlling at least one processing element of the above-described embodiments, for example, a computer-readable medium. The medium may correspond to a medium/media that enable storage and/or transmission of the computer-readable code.

The computer-readable code may be recorded in a medium or may be transmitted through the Internet. Examples of the medium include a read-only memory (ROM), a random-access memory (RAM), CD-ROMs, magnetic tapes, floppy disks, optical data storage devices, etc. The medium may also be a nontemporary computer-readable medium. Since the media can also be distributed networks, the computer-readable code can be stored, transmitted, and executed in a distributed fashion. Furthermore, for example, the processing element may include a processor or a computer processor, and the processing element may be distributed and/or included in one device.

As described above, in an X-ray imaging apparatus and a method of controlling the same in accordance with the one or more of the embodiments of the present invention, thickness information of an object is firstly measured, and a digital subtraction angiography (DSA) image of the object is obtained based on the thickness information so that, even when the object is moved, a motion artifact can be prevented from occurring in the DSA image.

Although a few embodiments of the present invention have been shown and described, it would be appreciated by those skilled in the art that changes may be made in these embodiments without departing from the principles and spirit of the invention, the scope of which is defined in the claims and their equivalents.

The invention claimed is:

1. A method of controlling an X-ray imaging apparatus including an X-ray generation unit, an X-ray detection unit, and an image processing unit, the method comprising:
   radiating, by the X-ray generating unit, X-ray having different energy levels sequentially to a phantom or an object;
   detecting, by the X-ray detection unit, the X-rays having the different energy levels transmitted through the phantom or the object;
   generating, by the image processing unit, a first phantom image and a second phantom image corresponding to the X-rays having the different energy levels transmitted through the phantom;
   generating, by the image processing unit, a first mask image and a second mask image corresponding to the X-rays having the different energy levels transmitted through the object;
   obtaining, by the image processing unit, thickness information of the object using the first phantom image, the second phantom image, the first mask image and the second mask image;
   generating, by the image processing unit, a reference phantom image in which the thickness information of the object is indicated;
   generating, by the image processing unit, a first live image corresponding to the X-rays radiated after a contrast medium is injected into the object and transmitted through the object;
   generating, by the image processing unit, a second live image based on the first live image, the reference, phantom image and the second phantom image; and
   generating, by the image processing unit, a final image using the second live image and the second mask image.

2. The method of claim 1, wherein the radiating the X-rays having the different energy levels sequentially to the phantom includes radiating al, low energy X-ray and a high energy X-ray to the phantom having a thickness equal to the thickness of the object and a mixture ratio of internal materials equal to an internal material mixture ratio of the object, before the contrast medium is injected into the object, and
   wherein the generating of the first phantom image and the second phantom image includes generating the first phantom image corresponding to the low energy X-ray and the second phantom image corresponding to the high energy X-ray.

3. The method of claim 1, wherein the radiating the X-rays having the different energy levels sequentially to the object includes radiating a low energy X-ray and a high energy X-ray to the object, and
   wherein the generating of the first mask image and the second mask image includes generating the first mask image corresponding to the low energy X-ray and the second mask image corresponding to the high energy X-ray.

4. The method of claim 1, wherein the obtaining of the thickness information of the object comprises:
   extracting an intensity value of each pixel of the first phantom image corresponding to each pixel of the first mask image, and indicating an area of pixels having same intensity value with an intensity value of a certain pixel of the first mask image on the first phantom image;
   extracting an intensity, value of each pixel of the second phantom image corresponding to each pixel of the second mask image, and indicating an area of pixels having same intensity value with an intensity value of a certain pixel of the second mask image on the second phantom image; and
   detecting a pixel positioned at an intersection of the indicated area of pixels of the first phantom image and the indicated area of pixels of the second phantom image by synthesizing the first phantom image and the second phantom image.

5. The method of claim 1, wherein the generating of the second live image comprises:
   extracting an intensity value of each pixel of the reference phantom image corresponding to each pixel of the first live image, and indicating an area of pixels having same intensity value with an intensity value of a certain pixel of the first live image on the reference phantom image;
   detecting a pixel positioned at an intersection of the area of pixels having the same intensity value in the reference phantom image and an area of in which the thickness information is indicated in the reference phantom image; and
   obtaining an intensity value of a pixel of the second phantom image corresponding to the pixel positioned at the intersection.

6. The method of claim 1, wherein the generating of the final image comprises:
   multiplying the second live image by a predetermined weighted value; and
   subtracting the second mask image from the second live image that is multiplied by the predetermined weighted value.

7. The method of claim 1, wherein the generating of the final image comprises:
   multiplying the second mask image by a predetermined weighted value; and
   subtracting the second live image from the second mask image that is multiplied by the predetermined weighted value.

8. An X-ray imaging apparatus comprising:
   an image generation unit configured to generate an X-ray image based on X-rays transmitted through an object;
   a thickness measurement unit configured to obtain thickness information of the object and generate a reference phantom image in which the obtained thickness information is indicated; and
   an image separation unit configured to generate a final image obtained by separating a material inside the object from the X-ray image using the reference phantom image.

9. The X-ray imaging apparatus of claim 8, wherein, before a contrast medium is injected into the object, the image generation unit generates a first mask image corresponding to a low energy X-ray transmitted through the object and a second mask image corresponding to a high energy X-ray transmitted through the object.

10. The X-ray imaging apparatus of claim 9, wherein the image generation unit generates a first phantom image corresponding to the low energy X-ray transmitted through a phantom image having a thickness equal to the thickness of the object and a mixture ratio of internal materials equal to an internal material mixture ratio of the object, and a second phantom image corresponding to the high energy X-ray transmitted through the phantom.

11. The X-ray imaging apparatus of claim 10, wherein the thickness measurement unit extracts an intensity value of each pixel of the first phantom image corresponding to each pixel of the first mask image, extracts an intensity value of each pixel of the second phantom image corresponding to each pixel of the second mask image, indicates an area of pixels having the same intensity value in each of the first phantom image and the second phantom image, and detects a pixel positioned at an intersection of the indicated area of pixels of the first phantom image and the indicated area of pixels of the second phantom image by synthesizing the first phantom image and the second phantom image, and then indicating thickness information of the pixel positioned at the intersection on the first phantom image, thereby generating the reference phantom image.

12. The X-ray imaging apparatus of claim 11, wherein, contrast medium is injected into the object, the image generation unit generates a first live image corresponding to the low energy X-ray transmitted through the object or to the high energy X-ray transmitted through the object.

13. The X-ray imaging apparatus of claim 12, further comprising an image estimation unit configured to extract an intensity value of each pixel of the reference phantom image corresponding to each pixel of the first live image, indicate an area of pixels having same intensity value with an intensity value of a certain pixel of the first live image on the reference phantom image, detect a pixel positioned at an intersection of the area of pixels having the same intensity value in the reference phantom image and an area of in which the thickness information is indicated in the reference phantom image, obtain an intensity value of a pixel of the second phantom image corresponding to the pixel positioned at the intersection, and then generate a second live image using the obtained intensity value of the pixel of the second phantom image.

14. The X-ray imaging apparatus of claim 13, wherein the image separation unit is further configured to multiply the second live image by a predetermined weighted value and subtracts the second mask image from the second live image that is multiplied by the predetermined weighted value, thereby generating the final image.

* * * * *